United States Patent [19]

Steller et al.

[11] Patent Number: 4,816,060

[45] Date of Patent: Mar. 28, 1989

[54] HERBICIDAL AQUEOUS COMPOSITIONS OF IMIDAZOLINONE HERBICIDES

[75] Inventors: William S. Steller, Fairless Hills, Pa.; Roger C. Keintz, Trenton, N.J.

[73] Assignee: American Cyanamid Company, Stamford, Conn.

[21] Appl. No.: 896,775

[22] Filed: Aug. 15, 1986

[51] Int. Cl.[4] .............................................. A01D 25/22
[52] U.S. Cl. ................................... 71/92; 71/DIG. 5
[58] Field of Search ............................. 71/92, DIG. 5

[56] References Cited

PUBLICATIONS

Adalla et al. Chem. Abst. vol. 93 (1980), 90069b.

*Primary Examiner*—Catherine L. Mills
*Attorney, Agent, or Firm*—Alice C. Brennan

[57] ABSTRACT

The present invention relates to aqueous compositions of imidazolinone acid herbicides.

9 Claims, No Drawings

HERBICIDAL AQUEOUS COMPOSITIONS OF IMIDAZOLINONE HERBICIDES

BACKGROUND OF THE INVENTION

The recent discovery of a potent new class of herbicidal compounds, known as the imidazolinone compounds, has resulted in considerable field testing of these compounds for various uses worldwide.

Novel imidazolinyl benzoic acids, esters and salts, their preparation and use are disclosed in U.S. Pat. Nos. 4,188,487; 4,297,128 and 4,554,013 and pending application for U.S. Letters Patent Ser. Nos. 579,224, and 629,296, while various novel pyridine and quinoline imidazolinone compounds are described in pending application for U.S. Letters Patent Ser. No. 382,041, and U.S. Pat. Nos. 4,647,301, 4,650,514, 4,608,079 and 4,701,208.

The free acids of these compounds may be represented in general by formula I below

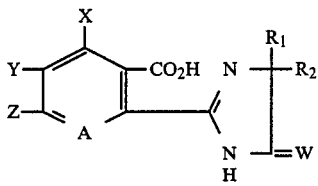

wherein
A is CH, N or N→O;
W is oxygen or sulfur;
X is H, halogen, methyl or hydroxyl;
Y and Z are each hydrogen, halogen, $C_1$-$C_6$ alkyl, hydroxyloweralkyl, $C_1$-$C_6$ alkoxy, $C_1$-$C_4$ alkylthio, phenoxy, $C_1$-$C_4$ haloalkyl, nitro, cyano, $C_1$-$C_4$ alkylamino, diloweralkylamino or $C_1$-$C_4$ alkylsulfonyl group; or phenyl optionally substituted with $C_1$-$C_4$ alkyl, $C_1$-$C_4$ alkoxy or halogen; difluoromethoxy, trifluoromethoxy, 1,1,2,2-tetrafluoroethoxy, $C_3$-$C_8$ straight or branched alkenyloxy optionally substituted with one to three halogens, or $C_3$-$C_8$ straight or branched alkynyloxy optionally substituted with one to three halogens; and, when taken together, Y and Z may form a ring which may optionally be substituted, in which YZ are represented by $-(CH_2)_n-$, $-(CH)_n-$, where n is an integer of 3 or 4, and when A is N or N→O YZ may also be $-(CH_2)_2-Q-$ or $-(CH)_2-Q-$, wherein Q is oxygen or sulfur, with the proviso that X is hydrogen;
$R_1$ is $C_1$-$C_4$ alkyl;
$R_2$ is $C_1$-$C_4$ alkyl or $C_3$-$C_6$ cycloalkyl; and when $R_1$ and $R_2$ are taken together with the carbon to which they are attached they may represent $C_3$-$C_6$ cycloalkyl optionally substituted with methyl.

Acids of formula I may be formulated as aqueous solutions of a water soluble salt of the acid, as they have limited solubility in non-protic organic solvents. The preparation of organic solvent emulsifiable compositions of formula I acids by utilizing $C_8$ to $C_{22}$ tertiary alkylamine salts of the acid which are soluble in organic solvents is described in pending application for U.S. Letters Patent of B. Cross and W. Steller, Ser. No. 734,212 filed May 15, 1985.

While aqueous solutions of imidazolinyl acid salts are suitable for a variety of general herbicidal uses, it has been found that upon aging for extended periods of time and/or exposure to elevated temperatures, that aqueous solutions of these acid salts exhibit loss of potency.

It is an object of this invention to provide novel aqueous compositions of water soluble formula I herbicidal acid salts which are physically and chemically stable for extended periods of time over a wide range of temperatures.

SUMMARY OF THE INVENTION

The present invention is novel aqueous herbicidal compositions comprising on a weight basis 1.0% to 45% of a water soluble salt of a formula I imidazolinone acid; 0 to 20% of urea; 0% to 30% of a nonionic surfactant; and sufficient water to total 100% which have been buffered with a sufficient amount of acid to have an initial pH in a range of about from pH 6 to pH 8.5.

DETAILED DESCRIPTION OF THE INVENTION

It has been found that the long term stability and stability at elevated temperatures of aqueous compositions of water soluble acid salts of formula I imidazolinyl salts is improved by stabilizing the initial pH of the aqueous compositions with sufficient amounts of a mineral or water soluble organic acid to a pH about equal to the pH of the formula I acid which is normally in a range of about pH 6 to pH 8.5 and preferably pH 7 to pH 7.5. Preferred acids for use in the compositions of the invention include hydrochloric acid, phosphoric acid, sulfuric acid, acetic acid, propionic acid and the like with acetic acid being most preferred.

Additionally it has been found the addition of urea as an antifreezing agent to aqueous compositions of the invention in amounts of from 15% to 20% on a weight basis also improves the freeze-thaw characteristics of the compositions of the present invention, in that any solids which form during freezing readily redissolve on standing. Prior reference to the use of urea to improve cold stabilization of aqueous pyrazolium salt compositions may be found in U.S. Pat. No. 4,529,436. Surfactants suitable for use in the compositions of this invention are in general non-ionic surfactants with polyoxyethylene glycols, polyoxyethylene sorbitan monolaurates and dialkylphenoxypolyethylineoxyethanols being preferred.

Salts of formula I compounds which find utility in the compositions of this invention are in general those which have sufficient water solubility to provide about 1% to 50% aqueous solution of the acid as the salt, with sodium, potassium, ammonium and water soluble organic ammonium being preferred and sodium, potassium, ammonium and isopropylammonium being most preferred.

The invention is further illustrated by the following non-limiting examples.

EXAMPLE 1

Preparation of Aqueous Herbicidal Compositions of Imidazolinyl Acid Salts

The formula I imidazolinyl acids listed in Table I below are added at ambient temperature to a stirred water solution containing 1.0 to 1.10 equivalents of the desired base and the desired quantity of urea and surfactant. The resulting mixture is agitated until complete solution of the acid is obtained. The pH of the solution is adjusted to the desired pH range by the addition of mineral or organic acids to the stirred solution followed by the addition of water to obtain the desired final concentration of ingredients.

Utilizing the above procedures yields the compositions listed in Table I below:

aqueous compositions which have their initial pH adjusted and stabilized by the addition of acid.

TABLE I

| Formula I acid | Salt | Composition | % w/w Active ingredient* | (Surfactant) | Urea | (Acid) | Water | pH |
|---|---|---|---|---|---|---|---|---|
| 2-(4-isopropyl-4-methyl-5-oxo-2-imidazolin-2-yl)quinoline-3-carboxylic acid | ammonium (1.3% w/w NH$_3$) | 1a | 16.46 | 1.0 (polyoxyethylene sorbitan monolaurate, 20 MEO**) | 15.0 | 0.7 (acetic) | 60.81 | 7.75 |
| | | b | 17.13 | 1.0 (polyoxyethylene sorbitan monolaurate, 20 MEO) | 15.0 | 0.7 (acetic) | 61.47 | 7.54 |
| | | c | 17.06 | — | — | 0.7 (acetic) | 76.93 | 7.56 |
| | | d | 18.8 | — | — | 0.7 (acetic) | 73.94 | 7.60 |
| | | e | 19.32 | — | — | 0.7 (acetic) | 73.15 | 7.2 |
| | | f | 19.67 | — | — | 0.7 (acetic) | 73.02 | 8.0 |
| | | g | 19.11 | — | — | 0.7 (acetic) | 72.89 | 8.3 |
| | | h | 18.32 | — | — | 0.7 (acetic) | 72.01 | 9.2 |
| 2-(4-isopropyl-4-methyl-5-oxo-2-imidazolin-2-nicotinic acid | isopropyl ammonium | 2a | 22.57 | 28.0 (polyethoxylated nonylphenol, 8–14 MEO) | — | — | 42.0 | 6.0 |
| | | b | 22.57 | 28.0 (polyethoxylated nonylphenyl, 8–14 MEO) | — | (HCl) | 42.0 | 7.0 |
| | | c | 22.57 | 28.0 (polyethoxylated nonylphenyl, 8–14 MEO) | — | — | 42.0 | 8.5 |
| | | d | 26.3 | — | — | (HCl) | 65.3 | 8.0 |
| | | e | 22.57 | 28.0 (polyethoxylated nonylphenyl 8–14 MEO) | — | — | 42.6 | 7.5 |
| | | f | 48.6 | — | — | — | 42.6 | 7.5 |
| | | g | 43.3 | — | — | — | 42.3 | 7.0 |
| | | h | 45.0 | — | — | — | 41.2 | 8.0 |
| | | i | 50.0 | — | — | — | 34.7 | 8.5 |
| 2-(4-isopropyl-4-methyl-5-oxo-2-imidazolin-2-yl) 5-methyl-nicotinic acid | ammonium | 3a | 21.8 | (—) | — | (acetic) | 70.0 | 7.0 |
| | | b | 21.8 | (—) | — | (acetic) | 70.0 | 9.0 |
| | | c | 21.9 | (—) | — | (acetic) | 70.0 | 9.0 |
| | | d | 22.0 | (—) | — | (acetic) | 68.6 | 10.0 |
| 5-ethyl-2-(4-isopropyl-4-methyl-5-oxo-2-imidazolin-2-yl)nicotinic acid | ammonium | 4a | 22.8 | (—) | — | 0.5 (acetic) | 71.2 | 6.5 |
| | | b | 21.8 | (—) | — | 1.4 (acetic) | 69.5 | 7.0 |
| | | c | 22.6 | (—) | — | 0.9 (acetic) | 69.0 | 7.4 |
| | | d | 20.3 | (—) | — | 3.7 (acetic) | 65.9 | 8.0 |
| | | e | 25.0 | (—) | 20.0 | 0.3 (acetic) | 47.7 | 7.1 |

*Calculated as the % free acid
**MEO is moles of ethylene oxide

EXAMPLE 2

Stability of Aqueous Herbicidal Compositions

Compositions prepared in Example 1 above are stored at 25° C., 37° C. and 45° C. Samples are withdrawn and the weight percent decomposition of the active formula I herbicide determined. The results of these experiments which are summarized in Table II below demonstrate the improvement in stability of

TABLE II

| Composition | pH | 25° C. % dec | 25° C. months | 37° C. % dec | 37° C. months | 45° C. % dec | 45° C. months |
|---|---|---|---|---|---|---|---|
| 1a | 7.75 | 0.2 | 12.0 | 21.0 | 12.0 | 6.5 | 3.0 |
| b | 7.54 | 3.8 | 12.0 | 24.0 | 12.0 | 12.4 | 3.0 |
| c | 7.56 | 7.8 | 24.0 | 16.0 | 12.0 | 3.5 | 3.0 |
| d | 9.60 | 0.3 | 12.0 | 0.3 | 12.0 | 4.5 | 3.0 |
| e | 7.2 | 1.5 | 6.0 | — | — | 5.2 | 3.0 |
| f | 8.0 | — | — | — | — | 4.1 | 3.0 |
| g | 8.3 | — | — | — | — | 29.2 | 3.0 |
| h | 9.2 | — | — | — | — | 87.0 | 3.0 |

TABLE II-continued

| Composition | pH | Weight % decomposition | | | | | |
|---|---|---|---|---|---|---|---|
| | | 25° C. | | 37° C. | | 45° C. | |
| | | % dec | months | % dec | months | % dec | months |
| 2a | 6.0 | 2.0 | 12.0 | 5.0 | 12.0 | 1.9 | 3.0 |
| b | 7.0 | 0.2 | 12.0 | 4.0 | 12.0 | 1.8 | 3.0 |
| c | 8.5 | 10.3 | 18.0 | 7.0 | 12.0 | 16.3 | 3.0 |
| d | 8.0 | 0.2 | 12.0 | 9.0 | 12.0 | 5.0 | 3.0 |
| e | 7.5 | 2.8 | 24.0 | 5.0 | 12.0 | 2.7 | 3.0 |
| f | 6.0 | 0.3 | 24.0 | 0.8 | 12.0 | 0.0 | — |
| g | 7.0 | 1.5 | 24.0 | 5.0 | 12.0 | 1.2 | 3.0 |
| h | 8.0 | 11.7 | 24.0 | 20.8 | 12.0 | 11.0 | 3.0 |
| i | 8.5 | 23.4 | 24.0 | 35.9 | 12.0 | 18.5 | 3.0 |
| 3a | 7.0 | 0.3 | 6.0 | 3.7 | 6.0 | 3.5 | 3.0 |
| b | 8.0 | 4.7 | 6.0 | 15.9 | 6.0 | 12.7 | 3.0 |
| c | 9.0 | 14.6 | 6.0 | 53.0 | 6.0 | 44.7 | 3.0 |
| d | 10.0 | 29.7 | 6.0 | 87.5 | 6.0 | 82.6 | 3.0 |
| 4a | 6.5 | 0.3 | 18.0 | 39.0 | 12.0 | 3.4 | 3.0 |
| b | 7.0 | 1.0 | 18.0 | 7.0 | 12.0 | 4.0 | 3.0 |
| c | 7.4 | 1.9 | 12.0 | 6.3 | 12.0 | 5.3 | 3.0 |
| d | 8.0 | 13.1 | 18.0 | 31.5 | 12.0 | 11.7 | 3.0 |
| e | 7.0 | 0.0 | 12.0 | 9.4 | 12.0 | 3.8 | 3.0 |

EXAMPLE 3

Effect of Urea on Redissolving Precipitated Solids

Compositions prepared by the procedure of Example 1 containing varying percentages of urea are cooled until precipitation of solids occurs. The samples are allowed to stand and are monitored until the temperature at which a complete solution is obtained and recorded. The results of these experiments are summarized in Table III below.

TABLE III

| Formula I acid | % Urea w/v | Redissolution Temp °C. |
|---|---|---|
| 2-(4-isopropyl-4-methyl-5-oxo-2-yl)-quinoline-3-carboxylic acid ammonium salt | 0 | 18 |
| | 6 | 5 |
| | 10 | 3 |
| | 15 | −5 |
| 2-(4-isopropyl-4-methyl-5-oxo-2-imidazolin-2-yl)-5-methyl nicotinic acid ammonium salt | 0 | −4 |
| | 5 | −7 |
| | 10 | −9 |
| | 15 | −11 |
| 5-ethyl-2-(4-isopropyl-4-methyl-5-oxo-2-imidazolin-2-yl)-nicotinic acid | 0 | 12 |
| | 10 | 9 |
| | 15 | 9 |
| | 20 | 1 |

What is claimed is:

1. An aqueous herbicidal composition comprising on a weight basis 1.0% to 45% of a water soluble imidazolinone acid salt selected from the group consisting of ammonium 2-(4-isopropyl-4-methyl-5-oxo-2-imidazolin-2-yl)quinoline-3-carboxylate, isopropylammonium 2-(4-isopropyl-4-methyl-5-oxo-2-imidazolin-2-yl)nicotinate, ammonium 5-ethyl-2-(4-isopropyl-4-methyl-5-oxo-2-imidazolin-2-yl)nicotinate and ammonium 2-(4-isopropyl-4-methyl-5-oxo-2-imidazolin-2-yl)-5-methylnicotinate; 0 to 20% urea; 0 to 30% nonionic surfactant and sufficient water to total 100% which has been buffered with a sufficient amount of acid to have an initial pH in a range of about pH 6 to pH 8.5.

2. A composition according to claim 1 wherein the acid used to adjust the pH is acetic acid; propionic acid; hydrochloric acid, phosphoric acid or sulfuric acid.

3. A composition according to claim 2 wherein the acid is acetic acid.

4. A composition according to claim 2 containing 15% to 20% by weight of urea.

5. A composition according to claim 4 having an initial pH in a range of pH 7 to pH 7.5.

6. A composition according to claim 5 wherein the formula I acid salt is ammonium 2-(4-isopropyl-4-methyl-5-oxo-2-imidazolin-2-yl)quinoline-3-carboxylate.

7. A composition accordng to claim 2 wherein the formula I acid salt is isopropylammonium 2-(4-isopropyl-4-methyl-5-oxo-2-imidazolin-2-yl)nicotinate.

8. A composition according to claim 5 wherein the formula I acid salt is ammonium 5-ethyl-2-(4-isopropyl-4-methyl-5-oxo-2-imidazolin-2-yl)nicotinate.

9. A composition according to claim 5 wherein the formula I acid salt is ammonium 2-(4-isopropyl-4-methyl-5-oxo-2-imidazolin-2-yl)-5-methylnicotinate.

* * * * *